United States Patent
Coffee

(10) Patent No.: US 7,977,527 B2
(45) Date of Patent: Jul. 12, 2011

(54) DISPENSING DEVICE AND METHOD FOR FORMING MATERIAL

(75) Inventor: Ronald Alan Coffee, Surrey (GB)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 12/823,205

(22) Filed: Jun. 25, 2010

(65) Prior Publication Data

US 2010/0286591 A1   Nov. 11, 2010

Related U.S. Application Data

(60) Division of application No. 11/711,378, filed on Feb. 27, 2007, now abandoned, which is a division of application No. 09/758,716, filed on Jan. 11, 2001, now Pat. No. 7,193,124, which is a continuation of application No. 09/230,171, filed as application No. PCT/GB97/01968 on Jul. 22, 1997, now Pat. No. 6,252,129.

(30) Foreign Application Priority Data

Jul. 23, 1996 (GB) .................................. 9615387.9
Sep. 26, 1996 (GB) .................................. 9620064.7

(51) Int. Cl.
*A61F 13/00* (2006.01)
(52) U.S. Cl. .................. 602/48; 602/41; 602/42; 239/3; 239/697
(58) Field of Classification Search ............ 602/48, 602/43, 2, 41, 42; 239/690, 692, 704; 238/3, 238/697
See application file for complete search history.

(56) References Cited

U.S. PATENT DOCUMENTS

| 4,043,331 | A | 8/1977 | Martin et al. |
| 4,565,736 | A | 1/1986 | Stein et al. |
| 4,644,018 | A | 2/1987 | Bowditch et al. |
| 4,657,793 | A | 4/1987 | Fisher |
| 5,146,730 | A | 9/1992 | Sadek et al. |
| 6,252,129 | B1 | 6/2001 | Coffee |

FOREIGN PATENT DOCUMENTS

| CA | 1 090 071 | 11/1980 |
| CA | 1 125 968 | 6/1982 |
| CA | 1 275 883 | 11/1990 |
| EP | 0 005 035 | 10/1979 |
| EP | 0 029 301 | 5/1981 |

(Continued)

OTHER PUBLICATIONS

U.S. Appl. No. 60/241,008, filed Oct. 18, 2000, Bowlin et al.

(Continued)

*Primary Examiner* — Kim M Lewis
(74) *Attorney, Agent, or Firm* — Frost Brown Todd LLC

(57) ABSTRACT

Described is a method of supplying an active ingredient to a location beneath the outer layer of skin or into soft tissue which includes the steps of providing a polymer-containing liquid comprising an active ingredient; subjecting the liquid issuing from an outlet to an electric field to cause the liquid to form at least one electrically charged jet that breaks up to provide charged fiber fragments or fibrils containing an active ingredient, the fiber fragments or fibrils being capable of sticking onto the outer layer of skin or soft tissue to supply the active ingredient beneath the outer layer of skin or soft tissue; and contacting skin with the fiber fragments or fibrils.

18 Claims, 7 Drawing Sheets

FOREIGN PATENT DOCUMENTS

Figure 1:
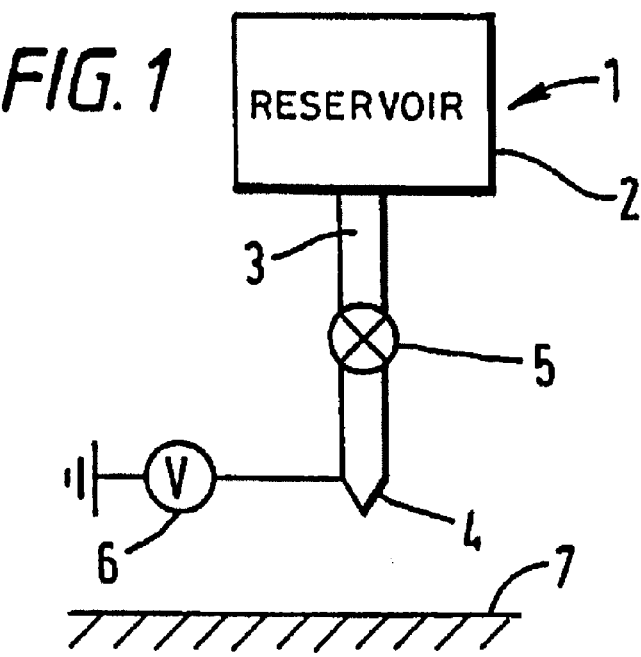

| | | |
|---|---|---|
| EP | 0 046 873 | 3/1982 |
| EP | 0 102 713 | 3/1984 |
| EP | 0 234 841 | 9/1987 |
| EP | 0 234 842 | 9/1987 |
| EP | 0 250 102 | 12/1987 |
| EP | 0 250 164 | 12/1987 |
| GB | 1 569 707 | 6/1980 |
| JP | 03 161402 | 7/1991 |
| WO | WO 94/13266 | 6/1994 |
| WO | WO 94/14543 | 7/1994 |
| WO | WO 94/12285 | 9/1994 |
| WO | WO 95/26235 | 10/1995 |
| WO | WO 9526235 A1 * | 10/1995 |
| WO | WO 01/27365 | 4/2001 |

OTHER PUBLICATIONS

Database WPI, Week 9544, Derwent Publications Ltd., London; AN 95-342809; XP002046663 & RU 2031661A (Ekomedservis) (Mar. 27, 1995).

Database WPI, Week 9602, Derwent Publications Ltd., London, AN 96-018586; XP002046662 & RU 2 034 534 A (Ekomedservis) (Oct. 5, 1995).

Database WPI, (Oct. 5, 1995).

International Search Report dated Nov. 21, 1997 for Application No. PCT/GB97/01968.

* cited by examiner

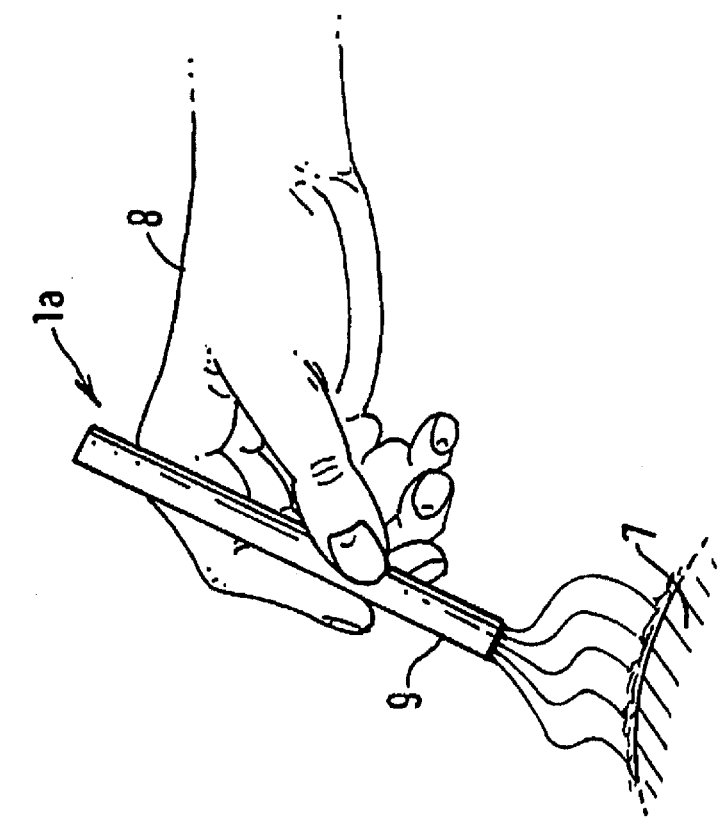
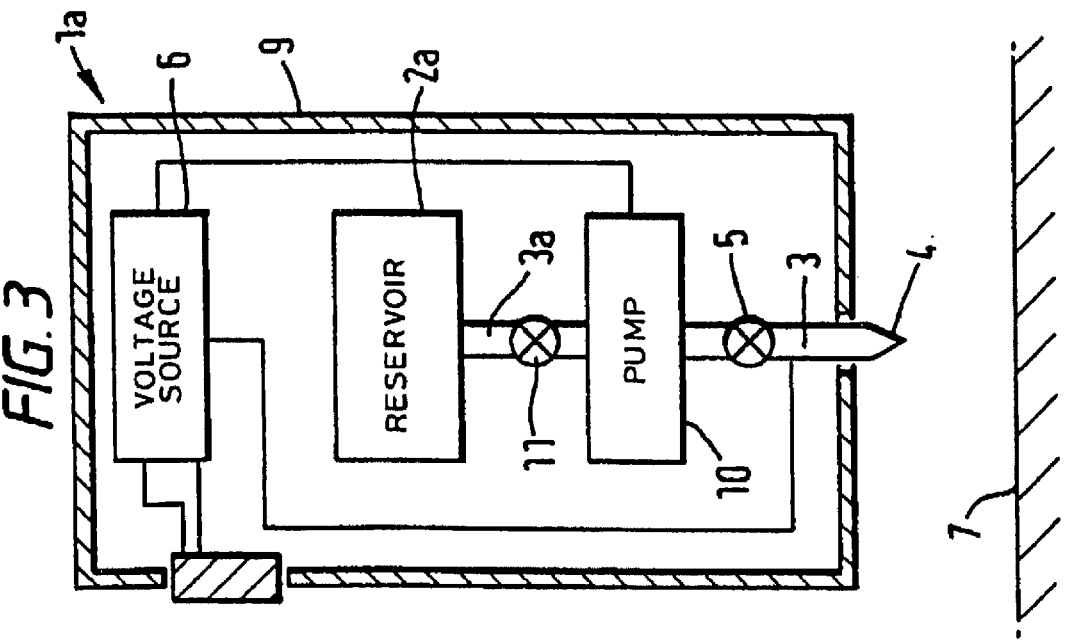

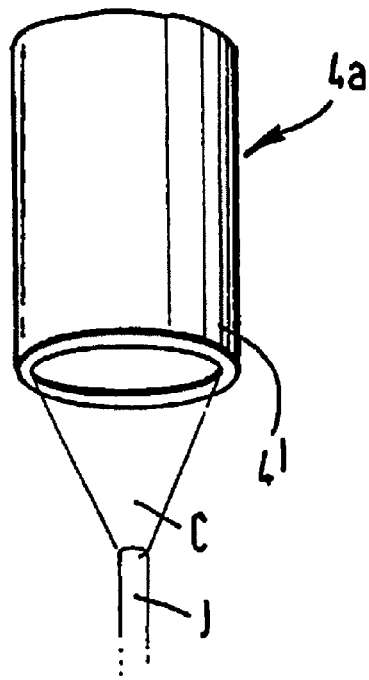
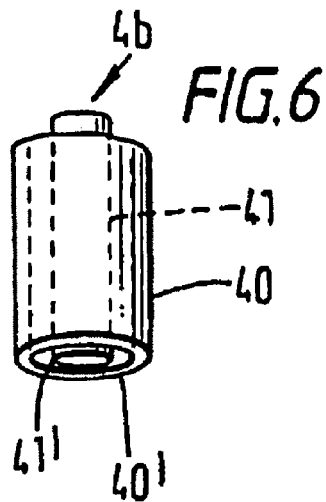
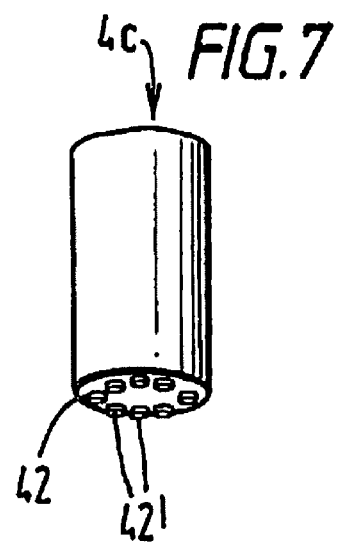
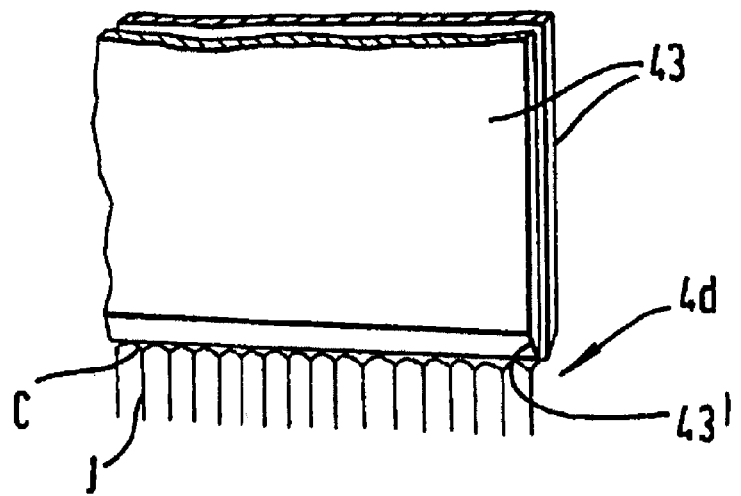

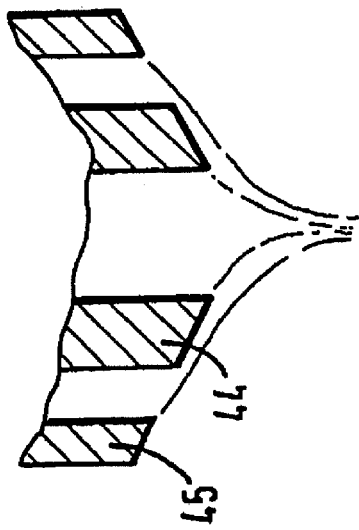
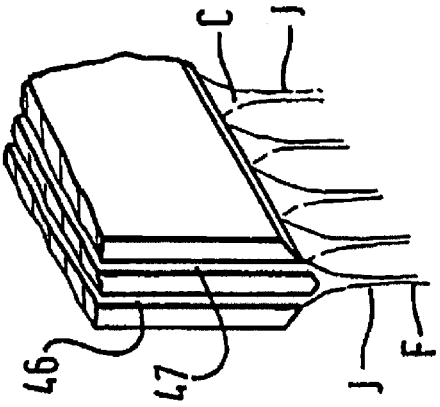
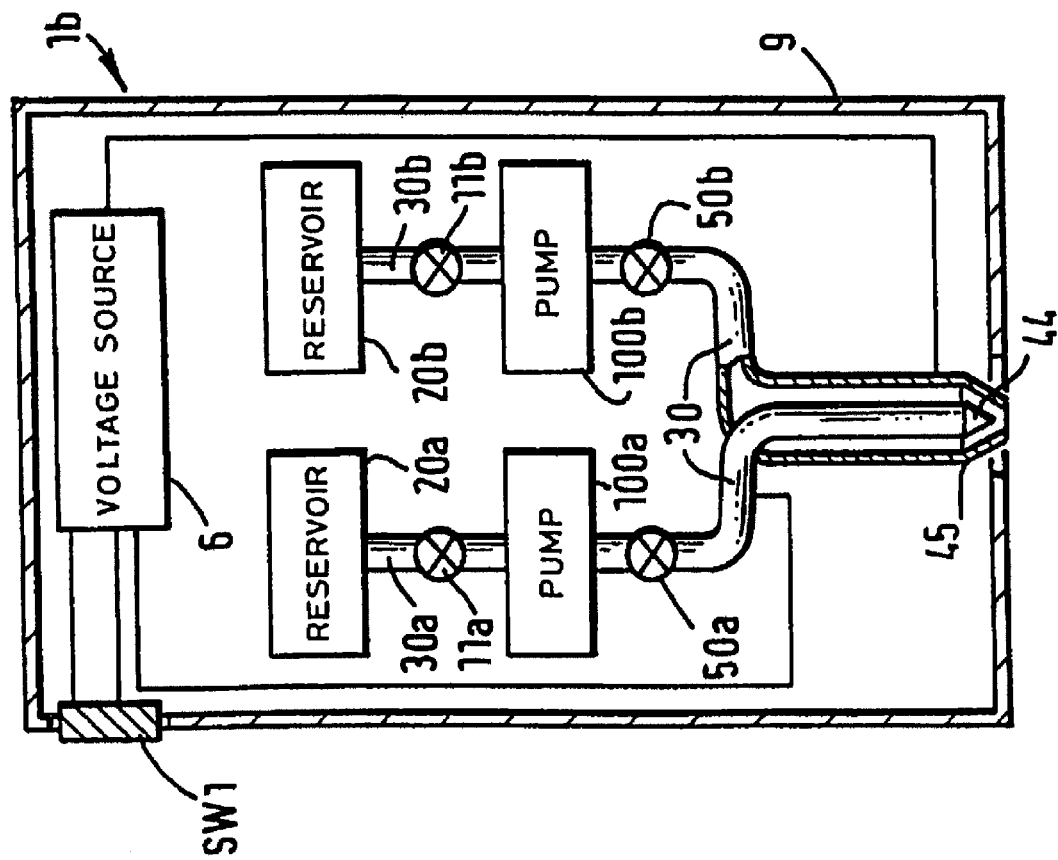

DISPENSING DEVICE AND METHOD FOR FORMING MATERIAL

CROSS-REFERENCE TO RELATED APPLICATIONS

This application is a divisional of 11/711,378, filed Feb. 27, 2007, which is a divisional of 09/758,718, filed Jan. 11, 2001, which is a continuation of Ser. No. 09/230,171, filed Jan. 21, 1999, which is a National Entry of PCT/GB97/01968, filed Jul. 22, 1997, which claims priority to GB 9615387.9, filed Jul. 23, 1996 and GB 9620064.7, filed Sep. 26, 1996.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION BY REFERENCE OF MATERIAL SUBMITTED ON A COMPACT DISK

Not Applicable

This invention relates to methods and devices for forming material. In one example, this invention relates to methods and devices for applying material to a surface, for example to an internal or external surface of an animal, for example for applying material to skin for use, for example, in the care or treatment of wounds or burns.

Various forms of aerosol devices for allowing material to be sprayed onto a surface such as the human skin are known, including aerosol devices for spraying wound care products onto wounds or burns. One such product is Savlon Dry (trade mark) which has been marketed in the UK by Zyma Healthcare and Ciba Geigy plc. Such products require the use of a gas propellant and in recent years the choice of gas propellants has become more limited because of the desire to avoid environmentally unfriendly compounds such as a chlorofluorocarbons or hydrocarbons. Also because small droplets and powder particles tend to be carried away from the target by the gas flow created when the propellant gas hits and is deflected by the target surface, such gas propelled sprays are generally designed to spray relatively large droplets or powder particles in order to achieve sufficient inertia to deposit the spray on its target surface. Such gas propelled products may run if sprayed too freely, especially where the spray produces large droplets. In addition, the packaging costs for such devices are high.

GB-A-1569707 describes a dispensing device for producing a spray or cloud of liquid droplets intended primarily for crop spraying. The process described in GB-A-1569707 produces liquid droplets by applying an electric field to a liquid emerging from an outlet in the vicinity of the surface so that the liquid becomes sufficiently charged that the net electric charge in the liquid as the liquid emerges into free space counteracts the surface tension forces of the liquid and the repulsive forces generated by the like electrical charges cause the liquid to be comminuted to produce a cone or jet which breaks into liquid droplets. The droplets produced by this device are charged close to their Rayleigh Limit and thus in use migrate quickly toward conductive surfaces of lower or zero potential. This technique of comminuting liquid is generally known as electrohydrodynamic comminution.

BRIEF SUMMARY OF THE INVENTION

In one aspect, the present invention provides a method and/or a device for forming solid, partially solid or gel-like matter such as fibres, fibrils or fibre fragments or segments, droplets or particles by an electrohydrodynamic process. The thus formed matter may incorporate or have a core of a different material which may be for example a biologically active ingredient or material. The formed matter may be applied to a surface or area such as, for example, the surface of the skin or a wound or burn or to a cavity, for example a body cavity. The body cavity may be the respiratory system of an animal such as a human being, where the electrohydrodynamic process produces matter that does not block the respiratory system.

Where the resulting matter or material is to be applied or supplied to a cavity or concave surface, then desirably the matter is at least partially electrically discharged before application or supply.

In another aspect, the present invention provides a method or device for forming a mat or web by electrohydrodynamically forming electrically charged fibres and/or fibrils in the vicinity of a surface or substrate. The present invention also provides a mat or web formed using an electrohydrodynamic process.

In an aspect, the present invention provides a method or device for applying material to a surface by supplying to an electrohydrodynamic site located in the vicinity of the surface liquid which is electrohydrodynamically processed at the site in such a manner so as to form matter comprising at least partially solid or gel-like fibres, fibre fragments or fibrils or particles which are charged and are electrostatically attracted to the said surface enabling a mat or web of randomly distributed fibres and/or fibrils and/or particles to be formed on the surface. The location at which the matter is deposited on the surface can be at least partially controlled by effecting relative movement between the surface and the matter.

In another aspect, the present invention provides a method of applying material to an exposed surface of an animal, for example to the skin or to a wound or burn or area exposed by a surgical procedure, which comprises producing material comprising at least one of electrically charged fibres, fibre fragments or fibrils or droplets or particles in the vicinity of the said surface area by an electrohydrodynamic process, so that the material deposits on the said area.

In another aspect, the present invention provides a method of forming fibre fragments or fibrils by supplying liquid to an electrohydrodynamic site and deliberately perturbing the cone or jet issuing from the comminution site to cause the resulting fibre to break up into fragments. The break up of the fibre may be promoted by pulsing the voltage used for the electrohydrodynamic process. The length of the fibrils may be controlled by adjusting the frequency of the pulses.

In another aspect, the present invention provides a method of forming at least partly solid droplets or particles by supplying liquid to an electrohydrodynamic comminution site.

In an example, the present invention provides a method of depositing fibres on a surface, for example to form a dressing for a surface area of an animal for example an area of skin, a wound or burn or for other therapeutic or cosmetic reasons, which comprises supplying liquid comprising polylactic acid having a molecular weight in the region of 144000, dissolved 10% by mass in acetone at approximately 10 milliliters per hour to an electrohydrodynamic comminution site located at about 5 to 10 cm above the surface.

In another example, the present invention provides a method of depositing fibres on a surface, for example to form dressing for a surface area of an animal for example an area of skin, a wound or burn or for other therapeutic or cosmetic reasons, which comprises subjecting liquid comprising a biocompatible polymer which may be bioresorbable or biodegradable polymer such as polylactic acid, polygylcolic acid, polyvinyl alcohol or polyhydroxybutyric acid to an electrohydrodynamic process in the vicinity of said area.

In an embodiment, the deposition process may be repeated one or more times to provide a number of layers of material comprising at least one of fibres, fibrils, droplets or particles on the surface. The polarity to which the material is charged may be reversed between deposition of different layers so as facilitate attraction between the layers.

The liquid used to produce the electrohydrodynamically formed matter may comprise a biologically active ingredient or component. Where the electrohydrodynamically formed material comprises fibrils, the fibrils may actually stick into the skin of soft tissue enabling delivery of the active component to a location beneath the outer layer of skin or soft tissue.

The liquid used may comprise a solution, suspension, microsuspension, emulsion, microemulsion, gel or even a melt which may contain an active component or components. Alternatively or additionally, the active component may be provided as a coating or a core of the fibre, fibril or particle. For example microcapsules, fibres or fibrils of a bioresorbable or biodegradable polymer may be formed which contain a biologically active ingredient. Material from the core of a fibre or fibril may be released from the ends of the fibre or fibril. Material from the core of a fibre, fibril or microcapsule may be released through the coating if the coating is permeable to the material contained within it or may be released as a result of the outer coating being breached, for example by chemical or enzymic attack which causes the outer coating to dissolve or degrade, by bioresorption or biodegradation of the coating, or as a result of temperature changes or application of pressure which causes the outer coating to rupture. The timing of the release may be controlled, for a given polymer, by controlling the thickness of the coating surrounding the core.

Possible biologically active components for topical application are pharmaceutical compounds such as analgesics, antiseptics, antibiotics, antifungals, antibacterials, antiparasitics, debridement agents such as proteolytic enzymes, biological products such as cells, and cytokines for stimulating cytokinetic activity to promote essential cell activities, for example, to stimulate dendritic growth, growth factors such as fibroblast growth factor (FGF), epithelial growth factor (EGF), transforming growth factor (TGF) and others that may be used to promote or otherwise control the sequence of events essential to natural tissue repair, DNA or other genetic material for gene therapy, cells, peptides or polypeptides, insulin, adjuvants, immune suppressants or stimulants, surface binding or surface recognising agents such as surface protein A, and surfactants. Where more than one layer of fibres, fibrils or droplets is deposited, then different active ingredients may be provided in different layers.

Fibres, fibre fragments or particles of biological material such as fibrin or collagen may be formed using a method embodying the invention. Also electret polymers may be used to act as nuclei or otherwise initiate interactive cellular and/or molecular events in tissue repair.

A number of electrohydrodynamic processing sites may be provided enabling different types of electrohydrodynamically formed matter to be deposited at the same time.

The deposited material may be used alone or in combination with a conventional bandage or dressing. As another possibility; where the material contains, for example, a therapeutic agent, the material may be deposited onto a conventional dressing to be applied to the skin.

In another aspect, the present invention provides a method or device for supplying comminuted material to the respiratory system of an animal, which comprises electrohydrodynamically comminuting liquid so as to produce a plurality of at least partially solid or gel-like fibrils or particles and supplying the fibrils or particles orally or nasally to the animal. The comminuted material is preferably at least partially electrically discharged before supply to the animal especially if it is to be delivered to the upper or lower reaches of the lungs rather than simply to the nasal or oral passages.

The fibrils or particles may comprise biologically active material, for example the fibrils or particles may comprise DNA encapsulated in or complexed with a lipid for transfecting cells or may, for example, contain or encapsulate matter such as peptides, polypeptides and other large biomolecules such as insulin or growth factor, and/or active pharmaceutical components for enabling delivery of the active component into the blood stream via the lung. This should provide a quicker route to the bloodstream than that provided by normal oral ingestion and avoids the need for injection of components which cannot be taken orally because of the gastric enzymes and acids present in the digestive system. Microcapsules or fibrils for oral ingestion of appropriate active components enabling slow release of those components may also be produced by electrohydrodynamic means by providing the active component as the core of the capsule or fibril.

BRIEF DESCRIPTION OF THE SEVERAL VIEWS OF THE DRAWINGS

Embodiments of the present invention will now be described, by way of example, with reference to the accompanying drawings, in which:

FIG. 1 shows schematically one example of a device for carrying out a method embodying the invention;

FIGS. 2*a* to 2*c* are schematic diagrams for illustrating the mechanisms by which at least partially solid or gel-like particles, fibrils and fibres, respectively, may be produced by a method embodying the invention;

FIG. 3 shows schematically another example of a device for carrying out a method embodying the invention;

FIG. 4 shows schematically use of the device shown in FIG. 3 to apply a dressing to the skin surface, a wound, burn or area exposed by a surgical procedure.

FIGS. 5 to 8 illustrate various different types of nozzles or outlets which may be, used in a method embodying the invention;

FIG. 9 shows a mat or web of fibres produced using a method embodying the present invention;

FIG. 10 shows substantially parallel fibres deposited on a surface using a method embodying the present invention;

FIG. 11 shows a part cross-sectional view of another example of a device for use in a method embodying the invention;

FIG. 12 shows a nozzle which may be used to produce composite material;

FIG. 13 shows a nozzle for producing material from a mixture of two different liquids; and FIG. 14 shows schematically another example of a device for carrying out a method embodying the invention.

DETAILED DESCRIPTION OF THE INVENTION

Referring now to the drawings, FIG. 1 shows schematically apparatus 1 comprising a container or reservoir 2 of liquid coupled by a supply pipe 3 to an outlet 4 via a flow regulating valve 5 of conventional form. The valve 5 may be a manually or electrically operable valve. A voltage source 6 supplying a voltage of typically 15 to 25 kV is coupled to the outlet 4 so as to cause liquid issuing from the outlet 4 to become charged. If the liquid is at least semiconducting (that is the liquid has a resistivity below about $10^9$ ohm-m), the voltage source 5 may be coupled to the liquid upstream of the outlet 4.

In use of the apparatus, a surface area 7 such as an area of the skin of an animal, for example an area of skin of a human being, is positioned a few centimeters, for example from 5 to 10 cm, below the outlet 4 as shown schematically in FIG. 1. The voltage source 6 is coupled to the outlet 4 by closing a switch (not shown in FIG. 1) and the flow regulating valve 5 opened so that liquid is supplied under gravity to the outlet 4. The liquid is selected to be biologically compatible, that is not harmful or detrimental to the animal when deposited on its skin or an open wound, and will typically have a resistivity in the range of from approximately $10^2$ to $10^8$ ohm-meters and a viscosity in the region of from 0.1 to 1000 Poise or greater with the viscosity being dependent on whether a fibre, fibre fragments or segments or particles are to be formed.

As described in the aforementioned GB-A-1569707 and an article entitled "Electrodynamic Crop Spraying" by R. A. Coffee published in Outlook on Agriculture Volume 10 No. 7 1981, liquid issuing from the outlet 4 is subject to an intense electrical field which establishes a standing wave along the surface of the liquid producing cusps or cones which emit jets of charged liquid.

The small perturbations which inevitably occur in the liquid jet cause the jet to become unstable and the net electrical charge in the liquid provides a repulsive force which acts against the surface tension forces in the liquid. This would normally be expected, as described in GB-A-1569707, to cause the liquid to break up into droplets which, because both they and the outlet 4 are similarly charged, are propelled away from the outlet 4 and each other so providing a spray or cloud of liquid droplets. The present inventors have, however, found that by selecting the liquid and controlling the conditions of the electrohydrodynamic process, the jet of liquid, rather than breaking up into liquid droplets, forms a solid or gel-like fibre or forms fibre fragments (fibrils) or non-liquid droplets or particles. In use of the apparatus shown in FIG. 1, the fact that the electrohydrodynamically produced material is charged and the animal body can effectively be considered earthed causes the material to deposit onto the surface 7 of the skin beneath the outlet 4. The material deposits swiftly, uniformly and gently by the energy contained in the electric field used to generate the material and will not overspray, nor become trapped in air streams and swept away from the target surface. One or more layers of such material may be deposited to provide a dressing to, for example, cover or protect, a wound or burn. This material being non-liquid should not cause the irritation which may arise from, for example, solvents if liquid droplets were applied to the skin.

Relative movement may be effected between the nozzle 4 and the surface 7, in this example the surface 7 may be moved, to enable coverage of a large area.

FIG. 2*a* illustrates the situation where the liquid supplied to the outlet or nozzle 4 forms a spray of solid droplets or particles D while FIG. 2*b* illustrates the situation where the liquid jet breaks up into fibrils FF and FIG. 2*c* illustrates the situation where the liquid jet J forms a fibre F.

FIGS. 2*a* to 2*c* show only one cone C and the associated jet J emanating from a nozzle 4. The actual number of cone and jets produced will, however, depend upon several factors, including the resistivity, permittivity and flow rate of the liquid, the dimensions of the outlet 4 and the applied electric field.

In order to form the solid or gel-like droplets shown in FIG. 2*a*, the liquid is selected or formulated so as to become non-liquid, that is at least partially solid or gel-like, after the liquid has been separated by the applied electric field into liquid droplets. Where the liquid includes a solvent, this may be achieved by, for example, selecting a liquid of such a volatility and viscosity and controlling the flow rate so that the solvent evaporates sufficiently to cause at least partial solidification or gellification only after droplet formation. Where the liquid is a melt which is held at an elevated temperature during supply to the outlet, then the liquid should be selected to have a melt temperature such that the liquid solidifies after liquid droplet formation. This may be facilitated by quenching using, for example, a cold inert gas or air stream.

To form the fibrils or fibre fragments shown in FIG. 2*b*, the liquid is selected or formulated and the flow rate controlled so that the liquid jet becomes at least partially non-liquid, that is solid or gel-like, before the liquid has been separated by the applied electric field into liquid droplets but so that the growth wave resulting from perturbation of the jet J remains sufficiently strong to inhibit formation of a fibre and causes the jet to break up into fibre fragments or fibrils FF. This may be achieved by selecting the liquid and flow rate so that the liquid begins to solidify (for example by evaporation in the case of a solution or by cooling in the case of a melt) before droplet formation and becomes relatively brittle so that the growth wave causes the nascent fibre to break into segments. Break up of the nascent fibre into fibrils may be facilitated by pulsing the voltage applied to the outlet 4 so as the create an energy pulse which sets up a resonant process to promote breaking up of the nascent fibre. Experiments have shown that the length of the fibrils is related to the pulse duration or frequency with, under ideal conditions, the fibril length being equal to the jet velocity divided by the pulse frequency so that, for example, if the jet velocity is 5 $ms^{-1}$ and a pulse frequency is 100 kHz is used, the fibrils should have a length of 50 μm. Fibrils having lengths in the region of, for example, tens of micrometers to a few centimeters may be produced, depending upon the particular liquid and electrohydrodynamic process conditions used.

In order to form the solid or gel-like fibre F shown in FIG. 2*c*, the liquid is selected so as to become non-liquid, that is at least partially solid or gel-like, after issuing from the outlet, and the growth wave resulting from perturbation of the jet is attenuated so that the jet does not break up but forms a continuous fibre which has a length determined by the time for which the electrohydrodynamic process is continued, that is the time for which the voltage is applied. Attenuation of the growth wave may be achieved by the incipient solidification and/or by the nature of the liquid. Fibre production may be achieved by, for example, selecting a liquid which is highly volatile or has a highly volatile component so that solidification by evaporation occurs very quickly before droplet formation. For example fibres may be formed using a liquid comprising a polymer which on solidification tends, because of its viscosity and/or polymer chain morphology, to resist growth wave development. Fibres may be formed using a relatively high molecular weight polymer, for example a polymer having a molecular weight in the region of 140000 or more. Where the liquid used is a melt then choosing a liquid which solidifies to a relativity plastic state should promote fibre formation.

The apparatus 1 shown in FIG. 1 uses a gravity feed to supply liquids to the outlet 4 which has the advantage of simplicity. It is most suitable for use in situations where the area of skin to which the dressing is to be applied can easily be moved beneath the outlet 4 or for use when the liquid to be supplied may be detrimentally affected by pumping.

FIG. 3 illustrates a part cross-sectional view of another form of apparatus 1a suitable for use in a method embodying the invention. The apparatus shown in FIG. 3 is, as illustrated schematically in FIG. 4, intended to be portable, in particular so as to be held in the hand 8 of a user.

The apparatus 1a shown in FIG. 3 comprises a housing 9 within which is mounted a reservoir 2a of the liquid to be dispensed. The reservoir 2a may be formed as a collapsible bag so as to avoid any air contact with the liquid being dispensed. The reservoir 2a is coupled via a supply pipe 3a to a pump chamber 10 which is itself coupled via the supply pipe 3 and the flow regulating valve 5 to the outlet 4 in a similar manner to that shown in FIG. 1. The voltage source 6 in this example is coupled to a user-operable switch SW1 which may be a conventional push button or toggle switch, for example. The voltage source 6 may comprise, for example a piezoelectric high voltage source of the type described in WO94/12285 or a battery operated electromagnetic high voltage multiplier such as that manufactured by Brandenburg, ASTEC Europe of Stourbridge West Midlands, UK or Start Spellman of Pulborough, West Sussex, UK and typically provides a voltage in the range of from 10 to 25 kV. Although not shown, a voltage control circuit comprising one or more resistor capacitor networks may be provided to ramp the voltage up smoothly. The reservoir 2a may be coupled to the pump chamber 10 by way of a valve 11 which may be a simple non-return or one way valve or may be an electrically or mechanically operable valve of any suitable type, for example a solenoid or piezoelectric valve, operable by a voltage supplied by the aforementioned control circuit.

The pump chamber 10 may comprise any suitable form of pump, which provides a continuous substantially constant flow rate, for example an electrically operable pump such as a piezoelectric, or diaphragm pump or an electrohydrodynamic pump as described in EP-A-0029301 or EP-A-0102713 or an electroosmotic pump as described in WO94/12285 or a mechanically operable pump such as syringe pump operated or primed by a spring biasing arrangement operable by a user.

In use of the apparatus 1a shown in FIGS. 3 and 4, the user first positions the apparatus over the area 7 to which the material is to be applied, then actuates the switch SW1 and the pump of the pump chamber 10 to cause, when the valves 5 and 11 are opened, a stream of liquid to be supplied to the outlet 4 whence the liquid is subjected to the applied electric field as described above with reference to FIGS. 2a to 2c, forming charged matter which deposits onto the said surface 7 which may be the skin or on or within a wound. The user may move the apparatus or device 1a relative to the area 7 to cover a large area. One or more layers may be formed in a manner similar to that described with reference to FIG. 1. The apparatus shown in FIGS. 3 and 4 has, however, the advantage that it is portable so allowing it to be used for, for example, first aid at the site of an accident and/or on relatively inaccessible areas of the body and does not rely on gravity feed.

Figure 2A:
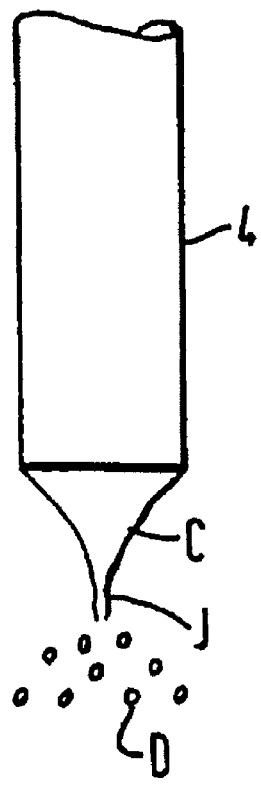
Figure 2B:
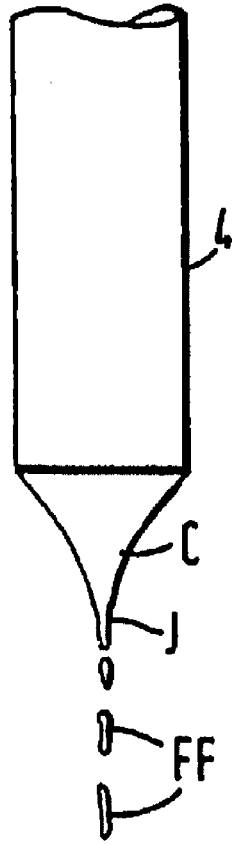
Figure 2C:
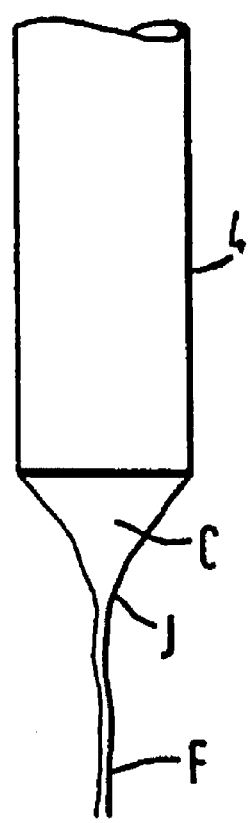

Various different forms of outlet or nozzle 4 may be used in the apparatus shown in FIGS. 1 and 3 and 4. FIGS. 5 to 8 illustrate schematically some examples. Another possibility is the fibre comminution site or nozzle described in WO95/26234.

The nozzle 4a shown in FIG. 5 comprises a hollow cylinder which is conductive or semiconductive material at least adjacent its end 4' where the voltage is to be applied in use and will in use produce one or more jets (one cusp or cone C and jet J are shown) depending upon the resistivity and flow rate of the liquid and the voltage applied to the outlet 4.

The nozzle 4b shown in FIG. 6 comprises two coaxial cylinders 40 and 41 at least one of which is conductive or semiconductive at least adjacent its end 40' or 41' where the voltage is applied and will in use produce a number of jets depending upon the resistivity and flow rate of the liquid and the applied voltage.

The nozzle 4c shown in FIG. 7 comprises a number of parallel capillary outlets 42 which are conductive or semiconductive at least adjacent their ends 42' where the voltage is applied. Each capillary outlet 42 will normally produce a single jet. The multiple nozzles shown in FIG. 7 have the advantage that blockage of one nozzle by relatively, viscous liquid does not significantly affect the operation of the device and also allow different liquids to be supplied from respective reservoirs to different ones of the nozzles.

The nozzle 4d shown in FIG. 8 comprises a slot-shaped nozzle defined between two parallel plates 43 which are conductive or semiconductive at least adjacent their ends 43' where the voltage is applied. The use of a slot nozzle when relatively highly viscous liquids are being used is advantageous because complete blockage of the nozzle is unlikely, as compared to the case where a relatively fine capillary nozzle is used, and a partial blockage should not significantly affect the functioning of the device because the liquid should be able to flow round any such partial blockage. The use of a slot-shaped nozzle outlet as shown in FIG. 8 also allows a linear array of jets and thus of fibres, fibrils or particles or non-liquid droplets to be formed.

Where, as discussed above, the liquid being used is sufficiently conductive to enable the voltage to be applied to the liquid rather than the nozzle then the nozzle may be formed of any suitable electrically insulative material which does not retain electrical charge for any significant length of time, for example glass or a semi-insulating plastic such as polyacetyl.

The nozzle shown in FIG. 7 is designed to produce a single jet per individual outlet 42. The nozzles shown in FIGS. 6 and 8 will in use produce a number of jets which extend generally along the electric field lines, with the number of jets depending upon, of course, the length of the slot (FIG. 8) or the diameter of the annulus (FIG. 6) and also upon the resistivity of the liquid, the flow rate and the applied voltage.

In the case of the cylindrical nozzle shown in FIG. 5, when the flow rate is high only one jet will be produced as shown. However, at low flow rates, the liquid tends to emerge from the outlet as a film which clings to the rim of the cylinder and there forms multiple jets in a manner analogous to the annular nozzle shown in FIG. 6.

Where the resistivity of the liquid is high, for example about $10^9$ ohm-m, some 10 or 20 jets, dependent upon the applied voltage and flow rate, may be formed per cm length of the nozzle, allowing the same number of fibres, for example, to be produced (spun). The applied voltage also affects the diameter of the resulting material. Thus, about 10 to 15 fibres of about 10 to 20 micrometers in diameter may be formed per cm length of the slot shown in FIG. 8 from a liquid having a resistivity of about $10^9$ ohm-m when the applied voltage is 15 kilovolts and a larger number, about 20, of fibres of smaller diameter may be formed per cm length of the slot when the applied voltage is 25 kilovolts. At liquid resistivities of, for example, $10^7$ ohm-m, some 5 to 10 fibres may be spun per cm length of the slot, dependent again on the applied voltage and flow rate, with again a larger number of thinner fibres being formed at higher voltages. The number of jets produced decreases but their diameter increases with increasing flow rate. By selecting the resistivity and viscosity of the liquid, the flow rate and the applied voltage, material, for example fibres or fibrils, with diameters from a few, about 10 nanometers (nm) to above 100 micrometers, typically $10^2$ to $10^4$ nm, may be produced. Similar results may be achieved using the hollow cylinder nozzle of FIG. 5 or the annular nozzle of FIG. 6.

The use of a liquid which is controlled to produce fibres is particularly advantageous for producing a wound or burn dressing because, as will be described below, deposition of the fibres onto the area being covered results in a network of crossing or interlinking fibres providing effectively an integral web or mat which has a high specific surface area and is thus highly absorbent to fluids, whilst being exceptionally light. Like a conventional dressing it enables good coverage over an area of skin so as, for example, to protect a wound but, unlike many conventional dressings, still enables, by virtue of the gaps between the network of fibres, air to pass through the dressing to the wound and pus and other detritus to pass from the wound, while preventing ingress of bacterial matter into the wound.

By controlling the diameters of the fibres in the manner described above and/or by controlling the number of layers of fibres, dressings having a range of thickness, fluid permeability and mechanical strength can be formed enabling the dressing to be adapted for use on different types of wounds and burns including wounds arising from severe trauma such as say motor vehicle accidents, battle wounds etc, and chronic wounds including lesions such as ulcerated veins as well as, where appropriate, surgically exposed tissue. The permeability of the dressing has been found to be a function of the diameters and spacing of the fibres and the motion of the nozzle over the deposition area during application.

Liquids which form short fibrils or solid droplets will not generally form a cohesive mat or web of fibres. However, liquids which form fibrils or solid droplets may be used in combination with conventional dressings or with dressings formed by fibres as discussed above, for example fibrils or solid droplets produced using a method embodying the invention may be deposited into or on a wound and then covered with one or more layers of fibres produced by method embodying the invention or by a conventional dressing.

Fibres, fibrils or droplets produced by a method embodying the invention may be deposited onto a substrate, such as a dressing, for later application to the skin, a wound, burn or the like.

Experiments have been carried out with a number of different polymers and solvents. It has been found that long chain heavy molecular structures facilitate fibre production while short chain length molecular structures tend to form fragments or solid droplets. Solvents which evaporate quickly during the jet flow may be used to facilitate formation of fibres. Suitable solvents may be, for example, methanol, propanol and water, methylene chloride, acetone and chloroform, depending upon the particular polymer used.

Experiments have been carried out in which the apparatus shown in FIG. 1 was used with water and hydrocarbon based solutions supplied to a slot-like nozzle of the type shown in FIG. 8 having a slot width of about 150 micrometers and a slot length of 2 cm. Liquid flow rates of from 1 to 10 microliters per second and voltages of from 10 kV to 15 kV were found to produce about 5 to 15 charged fibres per cm length of the slot with the fibres having diameters in the range of from 1 to 100 micrometers.

Figure 9:
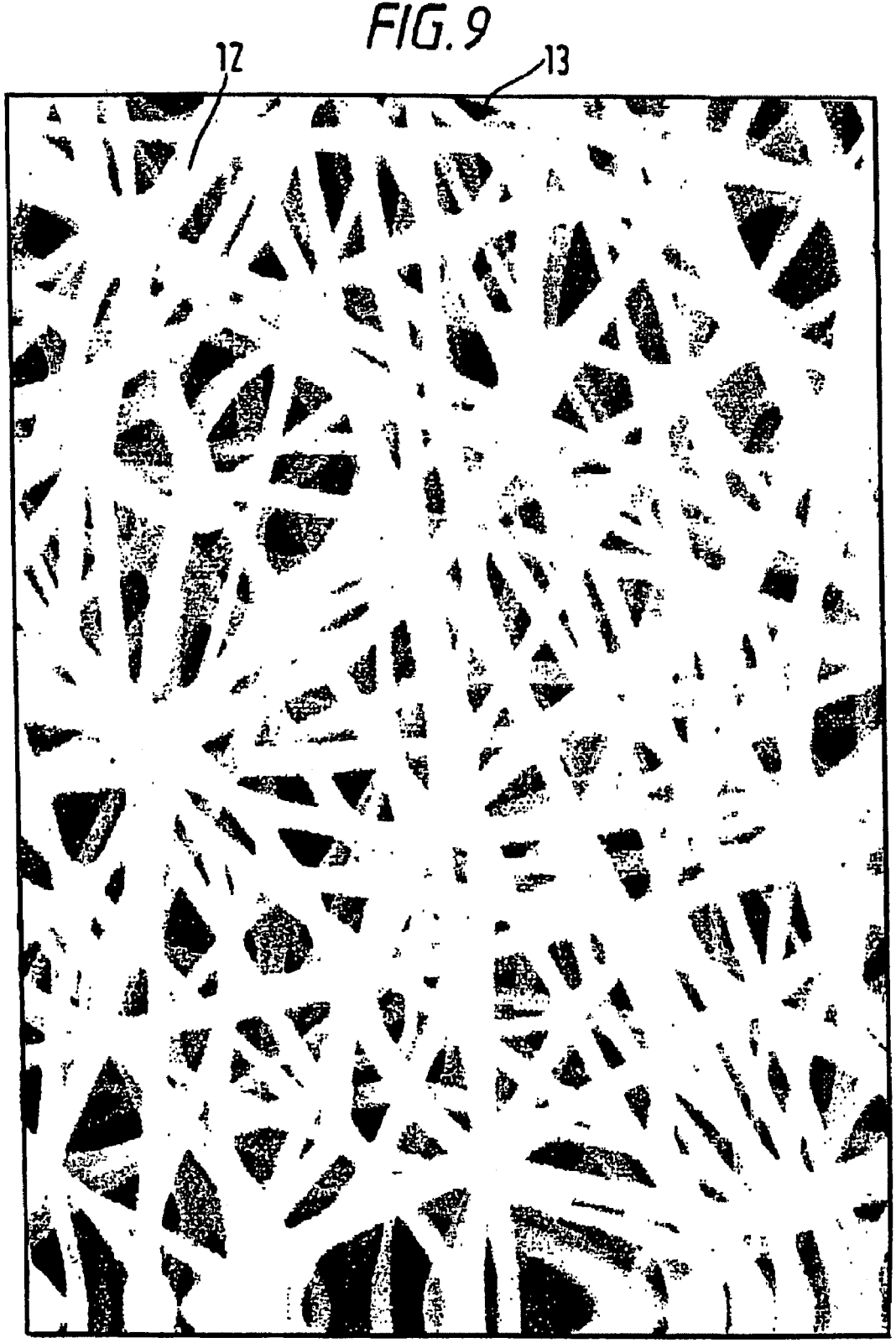

Fibres have been successfully spun with polyhydroxybutyric acid, a bioresorbable polymer, and polyvinyl alcohol (PVA), a polymer soluble in water and alcohols such as methanol or propanol, and pharmaceutical preparations for wound care, such as "New Skin" (trade mark) marketed by SmithKline Beecham which comprises nitrocellulose in an organic solution (in particular it comprises ethyl acetate, isopropyl alcohol, amyl acetate, isobutyl alcohol, denatured alcohol, camphor and nitrocellulose). "New Skin" is normally applied to scratches and light wounds with a rod or paddle because it is too viscous to be applicable by conventional spray devices. "New Skin" has however been successfully sprayed by a method embodying the invention to form fibres of approximately 0.5 to 5 micrometers diameter which deposited uniformly onto skin, resulting in a firm skin-like web-film. In one specific example neat (that is undiluted) "New Skin" was supplied at a flow rate of 4 milliliters per hour to a capillary nozzle of the type shown in FIG. 5 in the form of a 1.1 mm diameter thin-walled metal, generally stainless steel, tube. A voltage of 8.2 kV was applied to the nozzle which was located approximately 50 mm above an earthed deposition surface. Multiple fibres were formed and substantially uniformly deposited on the surface. Fibres have also been produced using undiluted "New Skin" (trade mark) with flow rates of from 1 milliliters per hour to 100 milliliters per hour.

Polyvinyl alcohol (PVA) has also been deposited in a similar manner to the "New Skin", using combinations of alcohol and water as solvent. Neat, undiluted PVA having a molecular weight of typically 15000 has been found to tend to form solid droplets when electrohydrodynamically processed while PVA having a molecular weight of about 140000 or more tends to form fibres. Low molecular weight PVA in a volatile solvent such as ethanol tends to break up into fibrils rather than continuous fibres. Thus, PVA having a molecular weight in the region of about 90000 to 140000 will tend to form fibrils and PVA fibrils having diameters of a few hundred nanometers and lengths of 0.5 to 10 mm have been produced.

In another experiment, an annular nozzle of the type shown in FIG. 6 was used to which a voltage of from 5 kV to 15 kV was applied. A 90% by volume solution of poly hydroxybutric acid (which is a bioresorbable polymer) β-methylene chloride was supplied at a flow rate of from 5 micro liters per second to 50 micro liters per second to the nozzle which was located at a distance of about 5 cm from human skin. A covering layer of fibres was formed on the skin with the fibres having diameters, dependent on the applied voltage and flow rate, in the range of from about 10 micrometers to about 50 micrometers.

In another example, the apparatus shown in FIG. 1 was used with a thin-walled, generally stainless steel, capillary nozzle of the type shown in FIG. 5 having a 1.1 mm external diameter. The reservoir was filled with polylactic acid having a molecular weight of 144000 dissolved 10% by mass in acetone and the flow regulator was controlled to provide a flow rate of 10 milliliters per hour. A voltage of 12 kV was applied to the nozzle which was located 8 cm away from and perpendicular to a flat earthed counter electrode provided to simulate a skin surface. This experiment was also repeated using a flow rate of 6.0 milliliters per hour and a nozzle voltage of 11.4 kV. The surface of the flat plate was covered by a network or mass of randomly distributed fibres having diameters typically in the region of from 2 micrometers to 7 micrometers.

The fibres deposit readily onto capacitive or earthed surfaces without any of the normal problems of applying very low mass high specific surface materials and the electrical field ensures that the fibres deposit swiftly, gently and substantially uniformly.

FIG. 9 shows a copy of an image produced by scanning electron microscope of a typical mat or web of fibres 12 on a plate 13. The fibres have, typically, a diameter of approximately 5 µm. The fibres shown in FIG. 9 are relatively randomly distributed because their relatively low mass, and thus low inertia, and high charge to mass ratio means that their movement and thus location of deposition on the surface is strongly influenced by the fact that they are all similarly charged fibres. This also results in the fibres crossing one another and possibly even blending together which should increase the overall mechanical integrity of the web or mat.

Figure 10:
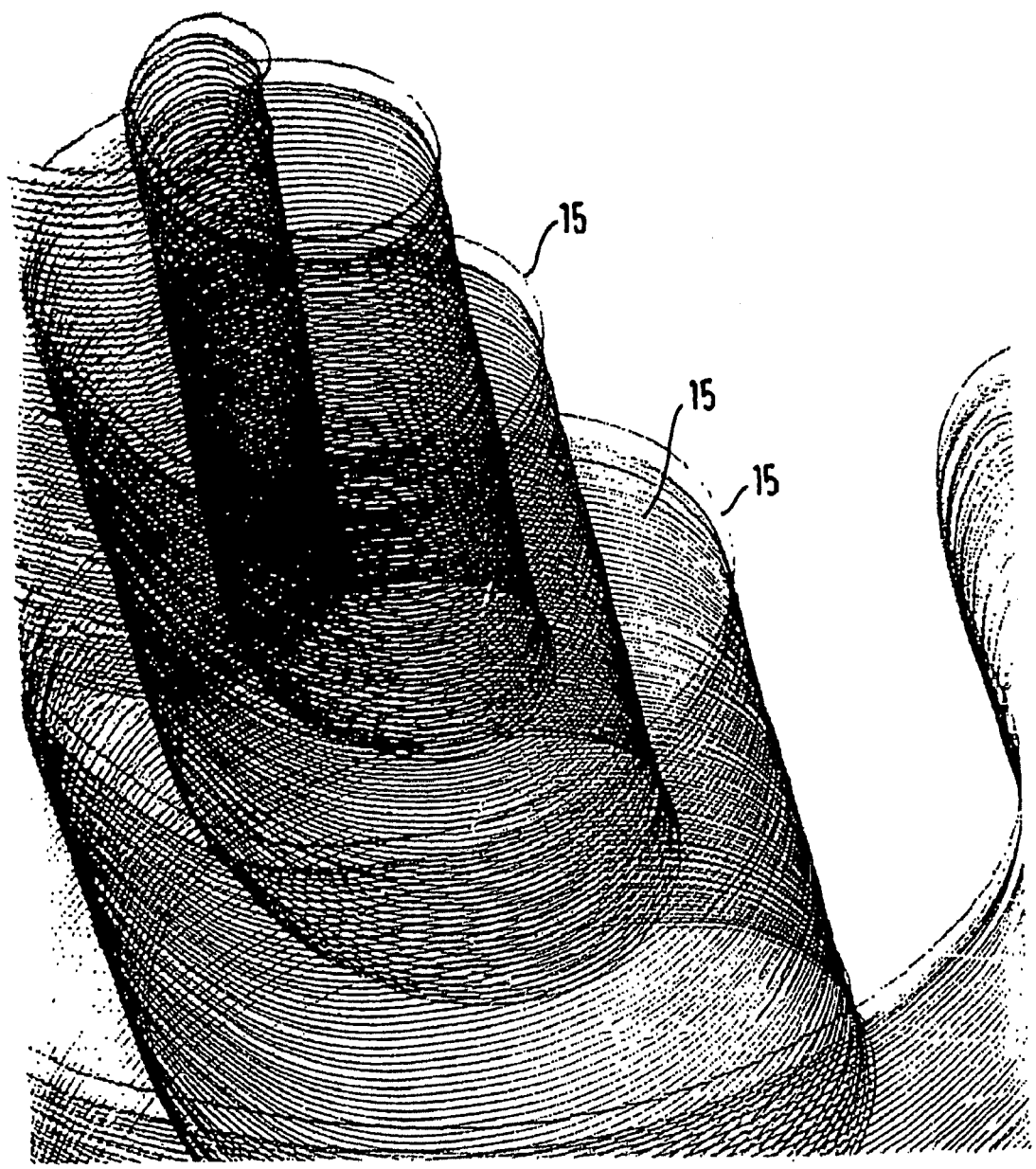

By increasing the mass of the fibres and thus their inertia, and reducing their charge to mass ratio, greater control can be achieved over the deposition of the fibres so that the location at which the fibres are deposited on the skin or wound can be controlled mainly by moving the nozzle relative to the skin or wound and by controlling the number of passes and pattern of movement of the nozzle over the surface. FIG. 10 shows an example of fibres 15 of about 50 to 100 micrometers in diameter deposited onto a substrate using a slot-shaped nozzle of the type shown in FIG. 8. As can be seen from FIG. 10, a single pass of the nozzle produces a set of approximately parallel tracks and, with two or more passes, a relatively dense material akin to a textile can be produced. Although the actual pattern shown in FIG. 10 was produced by depositing fibres of a heavy build viscous paint onto paper, it will be appreciated that similar results can be achieved using other material such as inert polymers of similar mass. The movement of the nozzle may be controlled to produce any desired pattern and that for example a woven texture could be simulated. Such fibres may be used, for example to form a bandage.

In the examples described above, the fibres, fibrils or droplets produced using the method embodying the invention consist simply of an inert polymer which may be a bioresorbable polymer such as polyhydroxybutyric acid, polyvinyl alcohol, polyglycolic acid or polylactic acid. Biologically active ingredients may, however, be added to the liquid before it is supplied to the outlet nozzle 4. In such cases, the liquid may comprise a solution, suspension, microsuspension, emulsion, microemulsion, gel or even a melt containing the active component or components. Possible active components are one or more of the following, namely pharmaceutical compounds such as analgesics, antiseptics, antibiotics, bactericides, antifungals, antiparasitics, anti-inflammatory agents, vasodilators (such as minoxidil which is believed to promote wound epithelialization and neovascularization), agents such as proteolytic enzymes for debridement and tissue repair promoting materials such as for example cytokines for stimulating cytokinetic activity to promote essential cell activities, for example to stimulate dendritic growth, growth factors such as fibroblast growth factor (FGF), epithelial growth factor (EGF), transforming growth factor (TGF) that are believed to reduce scarring and others that may be used to promote or otherwise control the sequence of events essential to natural tissue repair, cells, peptides, polypeptides, insulin, immune suppressants or stimulants and vaccines. Another possible active components are DNA or other genetic matter for gene therapy, surface binding or surface recognising agents such as surface protein A, and surfactants.

Where more than one layer of fibres, fibrils and/or particles is deposited, then different active ingredients may be provided in the different layers and different biologically active ingredients may be included in different fibres, fibrils or particles where a nozzle of the type shown in FIG. 7 is used. Also biologically active ingredients may be provided between layers, for example skin cells may be interspersed in or between layers.

The active ingredient may comprise an adjuvant that is a pharmacological agent added to a drug to increase or aid its effect or an immunological agent that increases the antigenic response.

Where the resulting material is in a form of fibrils, the fibrils may actually stick into the surface, for example skin or soft tissue, onto which they are deposited so enabling, for example, the supply of drugs and other biologically active agents beneath the skin or into the soft tissue, and may for example be used to carry DNA to cells.

FIG. 11 illustrates a modified form of the device shown in FIG. 3. The device 1b shown in FIG. 11 is essentially similar to that shown in FIG. 3 but comprises two reservoirs 20a and 20b each coupled by respective supply pipes 30a and 30b and possibly by non-return valves 11a and 11b to a respective pump chamber 100a and 100b coupled via a respective valve 50a and 50b to a respective liquid supply pipe 30 which terminates in a respective outlet 44 and 45 arranged so that the outlet 45 is coaxial with and extends around the outlet 44. FIG. 12 shows the outlets 44 and 45 on an enlarged scale. The device 1b shown in FIG. 11 allows different forms of liquid to be supplied to the electrohydrodynamic processing site provided by the outlets 44 and 45.

The reservoir 20a coupled to the inner outlet 44 may contain a supply of a biologically active ingredient such as a pharmaceutical or a solution of DNA for example, while the reservoir 20b coupled to the outer nozzle 45 may contain a supply of a polymer solution of the type discussed above, for example polyhydroxybutyric acid dissolved in methylene chloride. The device shown in FIG. 11 is operated in a similar manner to the device shown in FIG. 3. Thus, the switch SW1 is first activated to supply the required voltages, typically 10 to 25 kV, the flow regulating valves 50a and 50b are then opened to provide the required flow from each of the nozzles 44 and 45 and the pumps 100a and 100b and valves 11a and 11b, if present, activated to supply liquid to the respective nozzles 44 and 45. The outlets of the two coaxial nozzles are designed to promote laminar flow so that the polymer containing solution issues from the nozzle 45 so as to surround the other liquid.

By appropriate selection the molecular weight of the polymer and/or the volatility of the polymer solution, the liquids issuing from the combined nozzle can be caused to form a fibre or fibrils in which the biologically active ingredient forms a cylindrical centre core of the fibre or fibril or micro capsules in which the biologically active ingredient is completely encapsulated within the polymer and may still be in a liquid form.

For microcapsule formation it has been found preferable to reduce the percentage polymer in solution and to use a much reduced molecular weight polymer. For example a resin such as neoprene chlorinated rubber dissolved at more than about 10% by weight in trichloroethane will tend to spray fibres. However by decreasing the percentage polymer and/or using a less volatile solvent such as, for example, propylene glycol ether, microcapsules may be formed. Microcapsules have been produced using PVA of low molecular weight, for example a molecular weight of about 15000, dissolved to a dilution of between about 2.5 percent and 5 percent by volume in water or alcohol with a flow rate of about 1.0 microliters per second. Production of microcapsules may be enhanced by using two reactive monomers one of which is placed in each of the two liquids to react during comminution.

The composite products produced using the device shown in FIGS. 11 and 12 may be used to form a dressing in the manner described above where the composite product is in the form of fibres or long fibrils allowing for controlled release of the active ingredient as the bioresorbable polymer degrades. Where the composite products produced are fibres, fibrils or microcapsules, then these may be applied to the surface of the skin or into a wound in combination with, for example, a conventional dressing or a dressing produced from comminuted fibres. Material from the core of a fibre or fibril may be released from the ends of the fibre or fibril. Material from the core of a fibre, fibril or microcapsule may be released through the coating if the coating is permeable to the material contained within it or may be released as a result of the outer coating being breached, for example by chemical or enzymic attack which causes the outer coating to dissolve or degrade, by bioresorption or biodegradation of the coating, or as a result of temperature changes or application of pressure which causes the outer coating to rupture.

Composite products made up of three or more different layers of material may be formed by increasing the number of coaxial nozzles.

The outlet nozzle of the device shown in FIG. 11 may comprise a number of sets of coaxial outlet nozzles 44 and 45 in a manner similar to that shown in FIG. 7 for single outlet nozzles. This would allow different active ingredients to be supplied to different ones of the inner nozzles 44. The different active ingredients can thus be kept apart until actual use which is of particular advantage where the active ingredients react to form a product which itself has a low shelf life.

It will, of course, be appreciated that the apparatus shown in FIG. 1 could be modified in a manner similar to that shown in FIG. 11 for FIG. 3 to produce a device capable of forming cored fibres, fibrils or microcapsules.

As discussed above, the nozzle shown in FIG. 12 is deliberately designed to avoid mixing between the two liquids which are generally selected so as to be immiscible thereby enabling production of a cored fibre, fibril or microcapsule.

FIG. 13 shows an alternative form of nozzle which may be used in the apparatus shown in FIG. 11. The nozzle shown in FIG. 13 is a slot-nozzle similar to that shown in FIG. 8 but provided with two separate channels 46 and 47 coupled to respective ones of the liquid supply pipes so that each channel receives a different liquid. The outlets of the channels 46 and 47 are designed so as to create turbulence and therefore mixing of two liquids at the outlet. This arrangement may be used where, for example, it is desired to have some control over the amount of active ingredient which may be incorporated into a liquid or to combine two liquids which then react. A polyurethane foam has been formed by reacting a solution of urethane supplied via one of the nozzles with a blowing agent supplied by the other nozzle to spray a flexible foam deposit into a wound to form a cavity wound dressing. This arrangement has the advantage that the dressing will conform to the contours of a cavity wound and may be applied with clerical cleanliness without handling. Again, an active ingredient such as a pharmaceutically active ingredient may be incorporated into one of the two liquids or mixed with the two liquids.

The nozzle shown in FIG. 13 may also be used to, for example, bring reactive liquids together at the nozzle to deposit reacting or reactive product onto the skin or into a wound which should be of advantage where the reactive product has a very short lifetime and cannot be stored. For example, the nozzle shown in FIG. 13 has been used experimentally to produce a fibrin mat by supplying the enzyme thrombin to one channel and fibrinogen to the other channel.

As another possibility the device shown in FIG. 11 may be modified to provide two separate spaced nozzles and the voltage source arranged to charge the two nozzles to voltages of opposite polarity in a manner similar to that described in WO94/12285 so as to enable liquid droplets charged to one polarity to rapidly coalesce with droplets charged to the other polarity to form ultra-small particles of from sub-micron to a few tens of microns in diameter. Again, for example, ultra small droplets containing, for example the enzyme thrombin may be sprayed at one polarity so as to rapidly coalesce with droplets of the opposite polarity containing fibrinogen to deposit a fast reacting fibrin mat to cause blood clotting, for wound sealing or for adhesion.

A method embodying the invention may also be used to produce material capable of transfecting resident cells in situ with genetic material in order to regulate cell responses. For example, a method embodying the invention may be used to produce microcapsules comprising DNA encapsulated in a microcapsules or complexed with an appropriate lipid material for transfecting cells. Phospholipid microcapsules encapsulating DNA may be produced by a method embodying the invention. Other biological material such as proteins may be similarly encapsulated or complexed with an appropriate lipid material. Proteins may also be incorporated in the lipid layer. Surface binding or surface recognising agents such as surface protein A may be incorporated into microcapsules, especially phospholipid microcapsules, for selecting targets such as cancer cells, epithelial cells etc. Also, surfactants such as soya lecithin available from Sigma Pharmaceuticals may be incorporated in the outer surface of fibres, microcapsules or fibrils.

Fibres, fibrils or droplets or capsules produced by a method embodying the invention may be coated with substances such as surfactants such as soya lecithin or with, for example, DNA which is relatively sticky. This may be achieved by, for example, supplying the polymer containing liquid to the inner nozzle in FIG. 11 and supplying the coating material to the outer nozzle in FIG. 11. Alternatively, a separate spraying device, which may be a conventional or electrohydrodynamic spraying device, may be provided so as to direct, for example, an oppositely charged spray or cloud of the coating material into the path of the material produced by the apparatus shown in FIG. 1, 2 or 11, for example.

Figure 14:
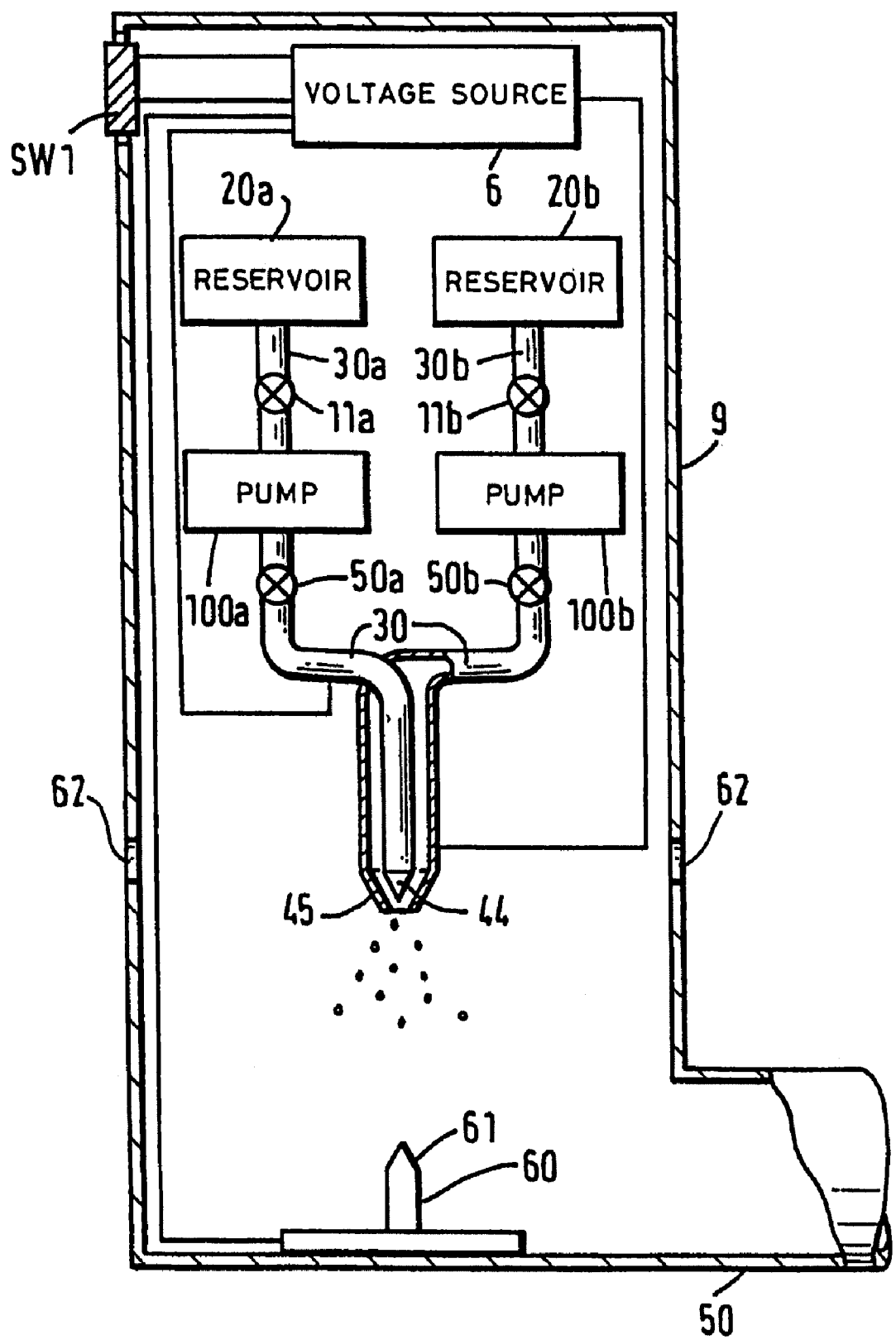

FIG. 14 illustrates schematically a modified form of the device shown in FIG. 11 which may be suitable for producing fibrils or microcapsules for inhalation. The device shown in FIG. 14 differs from that shown in FIG. 11 merely by the provision of air vents 62 and electrical discharge 60 means for discharging the fibrils or microcapsules and an outlet 50 adapted to receive a tube for insertion into the mouth or trachea of a user or to receive a mask to cover the mouth and nose of a user where both oral and nasal inhalation are required. The electrical discharging means may comprise, for example, an earthed discharge electrode 61 so as to produce gaseous ions of the opposite polarity to the charged fibrils or microcapsules so that the fibrils or microcapsules are discharged for inhalation by a user. The discharging means may be brought into operation by the active inhalation by the user as described in, for example, WO94/14543. The provision of the electrical discharge means enables the fibrils or microcapsules to be delivered to the upper or lower regions of the lungs rather than simply to the nasal passages. The actual location to which the fibrils or microcapsules are delivered can be controlled by controlling any residual electrical charge and the precise dimensions of the fibrils or microcapsules may be controlled by controlling the volatility, flow rate and voltage applied to the nozzle.

The material for oral delivery may comprise liposome encapsulated or complexed DNA for transfecting cells or may, for example comprise biologically active ingredients such as peptides, polypeptides and other large biomolecules such as insulin or growth factor, and active pharmaceutical components for enabling delivery of the active component into the blood stream via the lung. This should provide a quicker route to the bloodstream than that provided by normal oral ingestion and avoids the need for injection of components which cannot be taken orally because of the gastric enzymes and acids present in the digestive system.

Where a method embodying the invention is used to produce fibres, fibrils or microcapsules comprising a core of an active ingredient, the choice of coating material, the permeability and/or thickness of the coating may be adjusted to adjust the timing of release of the active ingredient. For example where the coating comprises a bioresorbable or biodegradable polymer, the half-life of the polymer may be controlled by controlling the permeability and/or thickness of the polymer coating by, for a specific formulation, controlling the flow rate and voltage.

A method embodying the invention may also be used to supply material to body cavities other than the respiratory system. Generally, for such use, the material will be at least partially electrically discharged before supply and means may be provided for forming an air or inert gas flow to assist the supply of the material to the body cavity. Where the body cavity is not easily accessible from the outside of the body, then the device embodying the invention may be mounted to an endoscope or like instrument enabling the device to be inserted into the body and to be positioned at the site where the material is required. The material may comprise any of the fibres, fibrils, particles and microcapsules mentioned above.

A method embodying the invention may also be used in a production process to form fibrils or particles comprising a biologically active ingredient and/or fibrils or microcapsules having a core of a biologically active ingredient which may themselves be encapsulated in conventional orally ingestible capsules, enabling, especially in the case of microcapsules, good control over the release of the active material.

A method and device embodying the invention may also be used for non-medical purposes. For example, coatings of fibres, fibrils, particles or microcapsules may be formed on substrates such as paper with good control of the thickness and uniformity of the coating. For example, adhesive may be deposited onto a substrate using a method embodying the invention.

Materials formed of two or more components which have only a short-shelf life when mixed together may be formed in a timely manner using a method embodying the present invention by encapsulating the respective components in respective fibres, fibrils or microcapsules so that mixing of the various components only occurs when the components are released from the encapsulating material by, for example, leaching through the encapsulating material, rupture by pressure being applied to the encapsulating material, temperature, or degradation, for example bioresorption or biodegradation, of the encapsulant. Such a method may be used to form, for example, two component adhesives which may be applied separately or simultaneously to a surface as cored fibres, fibrils or microcapsules by a method embodying the invention.

Other materials such as perfumes, insecticides, aromas, vapours, inks, dyes, lubricants, insect repellents etc., may be encapsulated in fibres, fibrils or microcapsules and deposited on a surface using a method embodying the invention, allowing the encapsulated ingredient to be released in a time-controlled manner as discussed in the previous paragraph, for example by application of pressure to the surface.

A method embodying the invention may also be used to produce a protective coating which may contain an active protective ingredient such as an anti-corrosive or a lubricant. For example, temporary protective coatings of delicate articles or articles liable to corrosion may be provided by depositing a web or mat on the surface of the article using a method embodying the invention.

Webs or mats formed using a method embodying the invention may also be sprayed or deposited over, for example, delicate crops such as grapes or strawberries so as to protect them from environmental effects such as frost, sun-damage, etc. Such a web may incorporate active ingredients such as insecticides, fungicides, miticides and the like to further protect the crop.

Generally, the capacitive nature of materials such as skin and the moisture content of the air should be sufficient for deposition onto a surface to occur simply by electrostatic attraction. However, where it is desired to deposit a large amount of material, then it may be necessary to earth the surface or to maintain it at a lower or opposite potential to the charged matter.

A method and device embodying the invention may also be used for supplying material to cavities other than body cavities and to concave surfaces. In such circumstances, the charged matter will generally be at least partially electrically discharged before it reaches the cavity or concave surface.

As used herein, the term "particle" includes solid, partially solid and gel-like droplets and microcapsules which incorporate solid, partially solid, gel-like or liquid matter. The term "active ingredient" means material which is compatible with and has an affect on the substrate or body to which it is to be applied and the term "biologically active ingredient" or "biologically active material" means material which is compatible with and has an affect (which may for example be biological, chemical or biochemical) on the animal or plant to which it is to be applied and includes, for example, medicaments such as proprietary medicines, pharmaceutical medicines and. veterinary medicines, vaccines, genetic material such as DNA, cells and the like.

The invention claimed is:

1. A method of supplying an active ingredient to a location beneath the outer layer of skin or into soft tissue, said method comprising the steps of:

(a.) providing a polymer-containing liquid comprising an active ingredient;

(b.) subjecting said liquid issuing from an outlet to an electric field to cause the liquid to form at least one electrically charged jet that breaks up to provide charged fiber fragments or fibrils comprising said active ingredient, said fiber fragments or fibrils being capable of sticking onto said outer layer of skin or soft tissue to supply said active ingredient beneath said outer layer of skin or soft tissue;

(c.) contacting skin with said fiber fragments or fibrils.

2. A method according to claim 1 wherein said liquid comprises an active ingredient selected from fibrinogen, thrombin, analgesics, antiseptics, antibiotics, bactericides, anti fungals, antiparasitics, anti-inflammatory agents, vasodilators, proteolytic enzymes, cytokines, fibroblast growth factor (FGF), epithelial growth factor (EGF), transforming growth-factor (TGF), cells, peptides, polypeptides, insulin, immune suppressants, stimulants, vaccines, and mixtures thereof.

3. A method according to claim 1, wherein said active ingredient comprises a material selected from DNA, peptides, polypeptides, or combinations thereof.

4. A method according to claim 1, wherein said active ingredient is encapsulated in or complexed with a lipid.

5. A method according to claim 1, wherein said active ingredient is a biologically active material capable of transfecting cells.

6. A method according to claim 1 wherein said method promotes tissue repair.

7. A method according to claim 1 wherein said fiber fragments or fibrils form a mat or web, wherein said mat or web incorporates said active ingredient.

8. A method according to claim 1 wherein said fiber fragments or fibrils form more than one layer.

9. A method according to claim 8 wherein said more than one layer comprise a first layer comprising a first active ingredient and a second layer comprising a second active ingredient.

10. A method according to claim 1 wherein said polymer is bioresorbable or biodegradable.

11. A method according to claim 1 wherein said polymer is selected from polyhydroxybutyric, polyvinyl alcohol, polyglycolic acid, polylactic acid, and mixtures thereof.

12. A method according to claim 1 wherein said fiber fragments or fibrils release said active ingredient as a result of dissolution or degradation of said fiber fragment or fibrils.

13. A method according to claim 12 wherein said dissolution or degradation occurs via a process selected from chemical or enzymatic attack, bioresorption, biodegradation, or combinations thereof.

14. A method according to claim 12 wherein said dissolution or degradation occurs as a result of temperature change.

15. A method according to claim 12 wherein said dissolution or degradation occurs as a result of application of pressure.

16. A method according to claim 12 wherein said dissolution or degradation is controlled by the thickness of a coating surrounding said fiber fragments or fibrils.

17. A method according to claim 1 wherein said fiber fragments or fibrils release said active ingredient as a result of dissolution or degradation of an outer coating on said fiber fragment or fibrils.

18. A method according to claim 1 wherein said fibrils or fiber fragments comprise electrically charged particles of a bioresorbable or biodegradable polymer carrying said active ingredient, wherein when said fiber fragments or fibrils, when contacted by chemicals or enzymes present in biological tissue or fluid, degrade via chemical or enzymatic attack such that said active ingredient is released into said skin or soft tissue.

* * * * *